(12) United States Patent
He et al.

(10) Patent No.: US 9,579,290 B2
(45) Date of Patent: Feb. 28, 2017

(54) METHOD FOR BANDING HARD CAPSULES USING HYDROXYPROPYLMETHYL CELLULOSE (HPMC) AS A BASE

(75) Inventors: Xiongwei He, Colmar (FR); Dominique Cade, Colmar (FR)

(73) Assignee: Capsugel Belgium NV, Bornem (BE)

( * ) Notice: Subject to any disclaimer, the term of this patent is extended or adjusted under 35 U.S.C. 154(b) by 2163 days.

(21) Appl. No.: 11/500,235

(22) Filed: Aug. 6, 2006

(65) Prior Publication Data
US 2007/0065501 A1    Mar. 22, 2007

(30) Foreign Application Priority Data

Aug. 12, 2005  (EP) ..................................... 05291729

(51) Int. Cl.
  *A61K 9/48*  (2006.01)
  *A61J 3/07*  (2006.01)

(52) U.S. Cl.
  CPC ............. *A61K 9/4808* (2013.01); *A61J 3/072* (2013.01); *A61K 9/4816* (2013.01)

(58) Field of Classification Search
  CPC ...... A61K 9/4808; A61K 9/4816; A61J 3/072
  See application file for complete search history.

(56) References Cited

U.S. PATENT DOCUMENTS

| | | | | |
|---|---|---|---|---|
| 3,071,513 A | * | 1/1963 | De Boer | A61J 3/072 424/454 |
| 3,198,708 A | | 8/1965 | Henkin et al. | |
| 3,493,407 A | * | 2/1970 | Greminger, Jr. et al. | 106/194.1 |
| 4,478,658 A | * | 10/1984 | Wittwer | A61J 3/072 156/246 |
| 4,756,902 A | | 7/1988 | Harvey et al. | |
| 4,922,682 A | | 5/1990 | Tait et al. | |
| 5,054,258 A | | 10/1991 | Tait et al. | |
| 5,302,373 A | | 4/1994 | Giacin et al. | |
| 5,968,538 A | * | 10/1999 | Snyder, Jr. | 424/404 |
| 6,887,307 B1 | * | 5/2005 | Scott | A61K 9/4816 106/205.01 |
| 2002/0000176 A1 | * | 1/2002 | Young | 106/194.2 |

FOREIGN PATENT DOCUMENTS

| | | | |
|---|---|---|---|
| EP | 074345 A2 | 7/1999 | |
| EP | 1072245 A1 | 7/1999 | |
| EP | 0 974 345 | 1/2000 | |
| EP | 0974345 A2 * | 1/2000 | ........... A61K 9/4883 |
| FR | 2788778 | 6/1999 | |
| WO | WO 2004/103338 A1 | 12/2004 | |

OTHER PUBLICATIONS

PubChem entry for "sorbitan monooleate" (CID 9920342), retrieved from <http://pubchem.ncbi.nlm.nih.gov/> on Jan. 28, 2014, pp. 1-4.*
PubChem entry for "sorbitan monolaurate" (CID 14926), retrieved from <http://pubchem.ncbi.nlm.nih.gov/> on Jan. 28, 2014, pp. 1-3.*
DOW Methocel® product literature; "Methocel Cellulose Ethers in Aqueous Systems for Tablet Coating," DOW® Chemical Company, Published Jul. 2002; pp. 1-32.*
Filing of liquids and semi-solids into hard two-piece capsules—Chapter 9—p. 182-183—Shionogi Qualicaps Co., Ltd.

* cited by examiner

*Primary Examiner* — David J Blanchard
*Assistant Examiner* — Ivan Greene
(74) *Attorney, Agent, or Firm* — Klarquist Sparkman, LLP

(57) ABSTRACT

The present invention provides a banding composition for hard capsules using hydroxypropylmethyl cellulose (HPMC) as a base comprising (1) low viscosity HPMC; (2) a component selected from the group consisting of methanol, ethanol, isopropanol, 1-propanol, acetone and/or ethyl acetate; (3) a surfactant; and (4) water; and a method for banding hard capsules using hydroxypropylmethyl cellulose as a base by using the banding composition described.

20 Claims, 2 Drawing Sheets

METHOD FOR BANDING HARD CAPSULES USING HYDROXYPROPYLMETHYL CELLULOSE (HPMC) AS A BASE

FIELD OF THE INVENTION

The present invention relates to hard capsules containing edible ingredients that usually comprise telescopically engaged capsule parts and more particularly to a method for banding such capsules which provides a tamper-resistant seal between the capsule parts and is also useful for liquid filled capsules by making the capsules liquid tight.

BACKGROUND OF THE INVENTION

The capsules to which the present method relates are well known and have been in broad use for many years. Such capsules are generally prepared from an edible natural substance such as gelatine or hydroxypropylmethyl cellulose and are telescopically joined so that they have a partial overlap of the cap-side wall with the body-side wall. Generally, such capsules are utilized in the pharmaceutical and food industries to hold edible and pharmaceutically active materials such as medicines, vitamin preparations and other edibles both solid and liquid.

One of the main targets when preparing capsules comprised of a body and cap is to avoid the propensity for leakage of the formulation through the gap between the cap and body of the capsule. In general, leakage can be minimized by product formulation and eliminated by sealing the two capsule parts together by sealing the junction between the cap and body by using a sealing liquid and/or by coating said junction with a layered solid material often termed banding.

While banding is successful against attempts at physical separation of the cap and body of the capsule, it is susceptible to disruption in the same way that the unmodified shell capsule components are.

Therefore, in the respective field of the art various attempts have been made to seal the cap and the body of the capsule directly to each other by means of a so-called "sealing fluid".

Prior art for capsule-sealing or banding is contained in the following patents:

U.S. Pat. No. 3,071,513 discloses a sealing fluid comprising a dispersion of an air-drying hydrophilic, film-forming polymer in an organic solvent. The application of the sealing fluid is by dipping the capsules.

U.S. Pat. No. 2,924,920 discloses a three-components mixture containing a polyhydric alcohol, a monohydric alcohol and water. This composition is used to seal capsules by a swelling technique. The process is designed to avoid solvent penetrating the overlap between capsule body and cap.

FR-A-2 118 883 discloses the use of a mixture of alcohol and water in an enteric coating process.

EP-A-0 152 517 discloses the use of thermal energy in conjunction with a mixture of alcohol and water to provide a seal between the cap and capsule body, wherein the fluid is positioned by capillary forces between the cap and the capsule body and subsequently heated in situ.

U.S. Pat. No. 4,756,902 discloses a method for sealing a gelatine capsule having a body and a cap comprising the steps of contacting the juncture of the cap and the body edge with a sealing fluid containing an alcohol-water solution maintained at a temperature of from 40 to 100° C. to form a liquid seal and continuous surfaced capsule; and applying a gelatine band to gird the capsule in the area of the liquid seal.

However, all the methods for banding hard capsules by using solutions suffer from several drawbacks. Thus, often capsule shells loose their strength when they are wetted by the water contained in the sealing solution leading to shell deformation, leaking and shell shrinkage at the sealing/banding area.

Hydroxypropylmethyl cellulose capsules are now well accepted as a non-animal alternative to the gelatine capsule. Its use is now very similar to the gelatine capsule; there are needs for tamper resistance as well as to tighten the capsules when filled with liquid formulas.

Furthermore, in general hard capsules using hydroxypropylmethyl cellulose as a base are treated on the external surface during their production with a gliding enhance agent to assure a good functioning performance on the high-speed filling equipment. Due to the presence of this agent, the sealing/banding edge often is irregular.

SUMMARY OF THE INVENTION

The inventors of the present invention therefore carried out several experiments to overcome the drawbacks mentioned above. As a result thereof the inventors of the present invention found that by using a specific banding composition comprising (1) low viscosity hydroxypropylmethyl cellulose (HPMC), (2) a component selected from methanol, ethanol, isopropanol, 1-propanol, acetone and/or ethyl acetate, (3) a surfactant and (4) water, an improved banding of hard HPMC capsules can be achieved. The present invention is based on said finding.

DETAILED DESCRIPTION OF THE INVENTION

Figure 1:
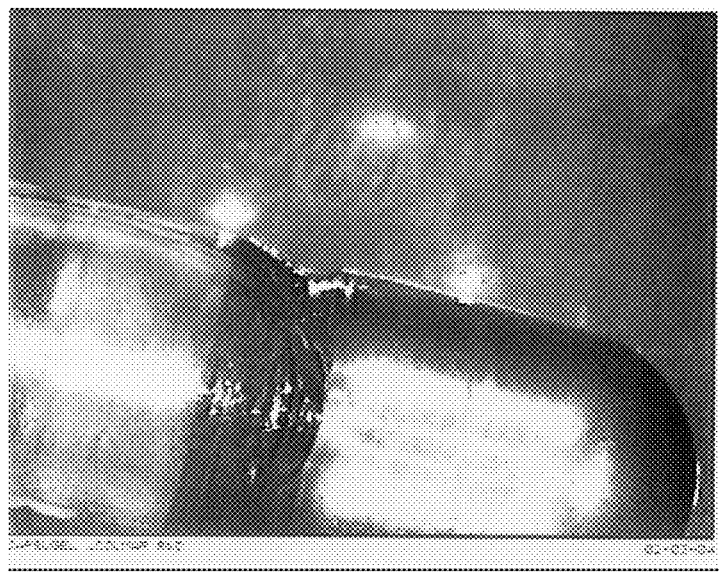
FIG. 1 is a photograph illustrating the result of banding with the solution of Comparative Example 1.

The present invention provides in a first aspect a banding composition for hard capsules using hydroxypropylmethyl cellulose (HPMC) as a base comprising the following components:
  (1) low viscosity HPMC;
  (2) a component selected from the group consisting of methanol, ethanol, isopropanol, 1-propanol, acetone and/or ethyl acetate;
  (3) a surfactant; and
  (4) water.

In a further embodiment the present invention provides a method for banding a hydroxypropylmethyl cellulose capsule having a body and a cap with the inner circumference of said cap at its edge being greater than the outer circumference of the capsule body, said method comprising: contacting the juncture of the cap and body edge with a banding composition comprising low viscosity HPMC, a component selected from the group consisting of methanol, ethanol, isopropanol, 1-propanol, acetone and/or ethyl acetate, a surfactant and water to form a continuous band or seal at least at the juncture of the cap and body edge of the capsule.

According to the present invention it has been found that by locally applying small amounts of a banding composition at the juncture between the body and the cap, an excellent seal without the leakage of the capsule filling can be obtained. At the same time the shell shrinkage at the juncture region and the formation of irregular edges of the banding can be avoided.

In the following, the banding composition according to the present invention is described in more detail.

The banding composition comprises as one of its components a low viscosity hydroxypropylmethyl cellulose (HPMC). According to the present invention the low viscosity HPMC to be used should be one such that a 2% aqueous solution of HPMC has a viscosity of usually not more than 15 centipoise (cP: 1 cP=1×10$^{-3}$ Pa·s=mPa·s) at 20° C., preferably of not more than 6 cP at 20° C. and more preferably of not more than 4.5 cP at 20° C.

As defined herein the viscosity of HPMC is not the viscosity of HPMC itself, but the viscosity of a 2% aqueous solution of HPMC throughout the specification and the claims.

Usually the low viscosity HPMC (1) is present in the banding composition claimed in a concentration of more than 15% by weight, preferably in an amount of more than 20% by weight based on the entire weight of the banding composition.

Component (2) to be used in the banding composition of the present invention is selected from the group consisting of methanol, ethanol, isopropanol, 1-propanol, acetone and/or ethyl acetate. In a preferred embodiment the component (b) is selected from acetone and/or ethanol.

Without being bound to any theory, at present the inventors of the present invention are of the opinion that component (2) used according to the present invention primarily acts in reducing the amount of water used in the banding solution and accordingly minimizing the risk for softening the capsule shell and therewith avoiding capsule deformation or shrinkage. A further action of component (2) can be seen in lowering the surface tension of the banding composition.

Usually the second component (2) is present in the banding composition claimed in a concentration of more than 20% by weight and less than 80% by weight, preferably in an amount of more than 30% by weight and less than 60% by weight based on the entire weight of the banding composition.

As a fourth component in the banding composition claimed according to the present invention water is used. Usually, demineralized water is used according to the present invention.

Water primarily acts in the banding composition claimed according to the present invention in promoting the sealing. The molten HPMC surface in the overlapping section of the capsule cap and body parts gives raise to a continuous seal without giving any shell deformation or shrinkage.

Usually the water (4) is present in the banding composition claimed in a concentration of more than 20% by weight and less than 80% by weight, preferably in an amount of more than 30% by weight and less than 60% by weight based on the entire weight of the banding composition.

The proportion of component (2) and water (4) usually is in a range of from 10:90 to 80:20% by weight, preferably in a range of from 40:60 to 60:40% by weight.

As a third component of the banding composition claimed according to the present invention, a surfactant is used. The surfactant (3) to be used according to the present invention includes amphoteric/zwitterionic surfactants, anionic surfactants, non-ionic surfactants and cationic surfactants. Preferably, those surfactants approved as food additive and/or pharmaceutical excipient are used according to the present invention.

Amphoteric surfactants useful according to the present invention can be described as a surface-active agent containing at least one anionic and one cationic group and can act as either acids or bases depending on pH. Some of these compounds are aliphatic derivatives of heterocyclic secondary and tertiary amines in which the aliphatic radical may be straight or branched and wherein one of the aliphatic substituent contains from 6 to 20, preferably from 8 to 18, carbon atoms and at least one contains an anionic water-solubilizing group, e.g. carboxy, phosphonate, phosphate, sulfate and sulfonate.

Zwitterionic surfactants can be described as surface-active agents having a positive and negative charge in the same molecule at all pHs. Zwitterionic surfactants can be best illustrated by betains and sultains. The zwitterionic compounds generally contain a quaternary ammonium, quaternary phosphonium or a tertiary sulfonium moiety. The cationic atom in the quaternary compound can be part of a heterocyclic ring. In all of these compounds there is at least one aliphatic group, straight chain or branched, containing from 6 to 20, preferably 8 to 18, carbon atoms and at least one aliphatic substituent containing an anionic water-solubilizing group, e.g. carboxy, sulfonate, sulfate, phosphate or phosphonate.

Examples of suitable amphoteric or zwitterionic surfactants include the alkali metal, alkaline earth metal, ammonium or substituted ammonium salts of alkylamphocarboxyglycinates and alkylamphocarboxypropionates, alkylamphodipropionates, alkylmonoacetate, alkyldiacetates, alkylamphoglycinates, and alkylamphopropionates, wherein alkyl represents and alkyl group having from 6 to 20 carbon atoms. Other suitable surfactants include alkyliminomonoacetates, alkyliminodiacetates, alkyliminopropionates, alkyliminodipropionates, and alkylamphopropyl sulfonates having between 12 and 18 carbon atoms, alkylbetains and alkylamidoalkylene betains and alkylsultains and alkylamidoalkylene hydroxysulfonate.

Anionic surfactants which may be used according to the present invention are those surfactant compounds which contain a long chain hydrocarbon hydrophobic group in their molecule structure and a hydrophilic group, including salts such as carboxylate, sulfonate, sulfate or phosphate groups. The salts may be sodium, potassium, calcium, magnesium, barium, iron, ammonium and amin salts of such surfactants.

Anionic surfactants include the alkali metal, ammonium and alkanolammonium salts of organosulfuric reaction products having in their molecular structure an alkyl or alkaryl group usually containing from 8 to 22 carbon atoms and a sulfonic, sulfuric acid ester group.

Examples of such anionic surfactant include soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as for example fatty acid taurides, N-acylamino acids such as for example acyl lactylates, acyl tartrates, acyl glutamates, acyl aspartates, alkyl oligoglucoside sulfates, protein fatty acid condensates (particularly wheat-based vegetable products) and alkyl(ether) phosphates.

Specific anionic surfactants which may be selected include linear alkylbenzene and alkane sulfates or sulfonates, such as decylbenzenesulfonate, undecylbenzenesulfonate, dodecylbenzenesulfonate, tridecylbenzenesulfonate, nonylbenzenesulfate, lauryl sulfate and the sodium, potassium, ammonium, and triethanol ammonium salts thereof.

The non-ionic surfactant(s) is (are) not critical and may be any of the non-ionic surfactants which are generally selected on the basis of compatibility, effectiveness and acceptability.

Examples of useful non-ionic surfactants include fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the non-ionic surfactants contain polyglycol ether chains, they may have a conventional homolog distribution, although they preferably have a narrow-range homolog distribution.

Preferred cationic surfactant to be used according to the present invention are the quaternary ammonium compounds and esterquats, more particularly quaternized fatty acid trialkanolamine ester salts.

Exemplary quaternary ammonium salts to be used according to the present invention include the alkylammonium halides such as cetyltrimethylammonium bromide, alkylarylammonium halides such as octadecyidimethylbenzylammonium bromide, N-alkylpyridinium halides such as N-cetylpyridinium bromide and the like. Other suitable types of quaternary ammonium salts include those in which the molecule contains either amide, ether or ester linkages such as octylphenoxyethoxyethyldimethylbenzylammonium chloride, N-(laurylcocoamidoformylmethyl)pyridinium chloride and the like.

Other very effective types of quaternary ammonium compounds which are useful according to the present invention include those in which the hydrophobic radical is characterized by a substituted aromatic nucleus as in the case of lauryloxyphenyltrimethylammonium chloride, cetylaminophenyltrimethylammoniummethosulfate, dodecylphenyltrimethylammoniummethosulfate, dodecybenzyltrimethylammonium chloride, chlorinated dodecylbenzyltrimethylammonium chloride and the like.

In a preferred embodiment the surfactant(s) to be used according to the present invention is selected from the group consisting of sorbitan fatty acid esters, sucrose fatty acid esters, polyoxyethylene fatty acid esters and sodium lauryl sulfate.

Usually the surfactant(s) (3) is (are) present in a concentration in the banding composition of from 0.001 to 1% by weight, more preferable in an amount of from 0.01 to 0.1% by weight based on the weight of the entire banding composition.

Furthermore the banding composition can comprise various additives such as coloring agents (e.g. dyes and pigments), opaque agents and/or flavours in conventional amounts.

In the following, the banding process according to the present invention is described in more detail.

Usually the time needed for banding is in a range from 1 seconds to 5 minutes. It should be noted that precise times for sealing are extremely difficult to define because sealing is not an instantaneous process but rather a continuous one and as will be seen from the following description the time of exposure to a banding composition claimed according to the present invention is only an approximation.

The preferred process for banding claimed according to the present invention usually involves the use of a sealing/banding machine to provide the liquid banding and in a particularly preferred aspect a label band can be positioned over the liquid-sealed area as a second seal.

For example a capsule-sealing machine employing a turntable with radially aligned, capsule-engaging slots can be used.

Usually the application of the banding composition to the capsule will be carried out at room temperature. Thereafter the sealed capsules are subjected to a drying step usually at room conditions for example by forced air-drying for at least 12 hours.

The banding composition usually is essentially evenly distributed between the overlapping sections of the cap and body parts of the HPMC capsule.

In a preferred embodiment of the second aspect the method comprises a further step of aligning the cap edge to surround the body edge of the capsule to be sealed prior to said contacting step.

Furthermore, preferably during the application of the banding composition at the juncture between the body and the cap, the capsule body and cap are simultaneously spun.

As mentioned previously a subsequent banding step can be carried out the success of which of course is dependent on the dryness of the capsule in the area where the band is to be applied. This area, which is at the time of banding a part of a continuous capsule surface, is where the previous sealing occurred.

While virtually no fluid after sealing is present on the HPMC capsule, a positive drying step can be performed for example by passing the capsules through a low humidity forced air tunnel when banding is also carried out.

If subsequent banding is not performed, the capsule surface still must be dry but this can occur by subjecting the capsules as mentioned above to a drying step.

With respect to the capsule shell composition of the HPMC capsules to be banded according to the present invention, the capsule shell composition usually comprises hydroxypropylmethyl cellulose (HPMC) as a water-soluble cellulose derivative base, optionally a gelling agent which usually is a hydrocolloid like carrageenan, gellan gum, alginates, locust been gum, etc. and optionally a co-gelling agent which usually is an alkali metal or alkaline earth metal ion like a potassium ion.

Furthermore the capsule shell composition can comprise various additives such as a coloring agents (e.g. dyes and pigments), opaque agents and flavours in conventional amounts.

The HPMC capsule parts to be used according to the present invention usually are prepared by a well-known dipping technique as used in the manufacture of conventional gelatine capsule shells. More particularly, HPMC capsules usually are prepared by immersing moulding pins into an immersion solution comprising HPMC, withdrawing the pins from the solution with the solution adhering to the periphery of the pins, drying the adhering solution to form capsule shells (body or cap), and removing these shells from the pins. The shells are cut to a suitable size, if necessary. A pair of body and cap shells thereafter are made to form a capsule.

EXAMPLES

Examples of the invention are given below by way of illustration and not by way of limitation. As is true for the rest of the application document, chemical terms and abbreviations have their normal and customary meanings unless otherwise indicated. All percents are by weight. Furthermore with the examples the three key elements of the invention are exemplified:

1. Use of low viscosity hydroxypropylmethyl cellulose,
2. Use of a blend water and component (2) to minimize the risk for softening the cap shell and avoiding the capsule deformation and/or shrinkage,
3. Addition of one or more surfactants to improve the compatibility between the banding solution and the capsule surface to obtain a better banding edge.

The examples are also supported by the drawings:

FIG. 1 shows the results of banding with the solution of comparative example 1.

Figure 2:
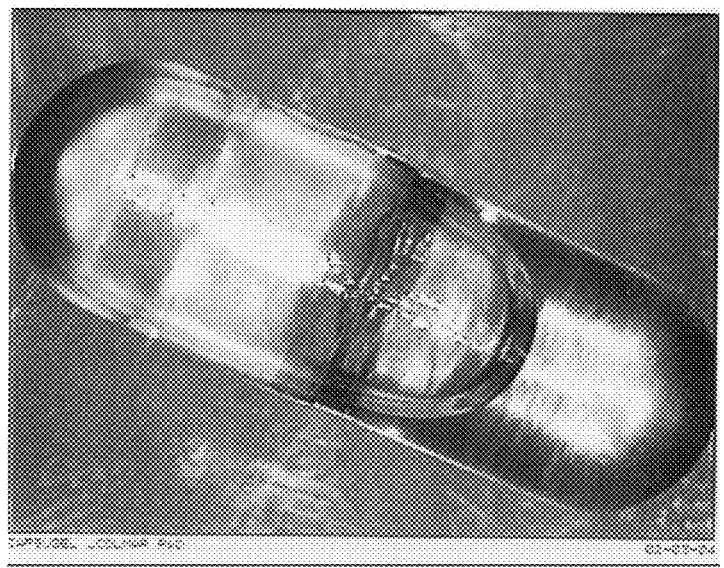
FIG. 2 is a photograph illustrating the result of banding with the solution of Comparative Example 2.

FIG. 2 shows the results of banding with the solution of comparative example 2.

Figure 3:
FIG. 3 is a photograph illustrating the result of banding with the solution of Example 1 according to an embodiment of the present disclosure.

FIG. 3 shows the results of banding with the solution of example 1 of the instant invention.

Example 1 and Comparative Examples 1 and 2

Three banding compositions with the compositions listed in the table below are prepared. Comparative banding compositions 1 and 2 serve to illustrate the benefits of the present patent composition. In order to facilitate the observation on the banding quality, a small quantity of patent blue V was added to the banding composition.

| Banding Solution | Comparative Example 1 | Comparative Example 2 | Example 1 |
|---|---|---|---|
| HPMC with viscosity of 3 cps | 24% | 24% | 24% |
| Surfactant: sorbitan monolaureate | No | No | 0.024% |
| Solvent | Water | Ethanol/Water = 50/50 | Ethanol/water = 50/50 |

The banding operations of HPMC capsules of size 0 filled with sunflower oil were performed on a capsule banding equipment MG2 by using these three banding compositions at room temperature. After drying at room conditions, the sealed capsules were equilibrated at 22° C./45% RH for 24 hours. Then the leaking level was checked and the sealed capsules were evaluated by a compression test. The compression test consists of pressing the banded capsules one by one on an Instron until to its breaking or leaking. The maximum loading force (average of 10 capsules tested) is reported.

The results regrouped in the table below and in the pictures of FIG. 1, FIG. 2, and FIG. 3 reveal that only the banding composition according to the present invention allows a banding of quality.

| Banding Solution | Comparative Example 1 | Comparative Example 2 | Example 1 |
|---|---|---|---|
| Leaking level | 14% | 0% | 0% |
| Compression test: maximum loading (N) | 45 | 253 | 234 |
| Observation | Shrinkage at banding area | Irregular Banding edge | Good banding: regular banding edge, no shrinkage |

The invention claimed is:

1. A method for banding a hydroxypropylmethyl cellulose (HPMC) hard capsule having a body and a cap with the inner circumference of said cap at its edge being greater than the outer circumference of the capsule body, said method comprising:
   providing said HPMC hard capsule; and
   contacting the juncture of the cap and body edge of said HPMC hard capsule with a banding composition, the banding composition comprising:
   (1) low viscosity HPMC present in the banding composition in an amount of more than 15% by weight based on the entire weight of the banding composition, the low viscosity HPMC having a viscosity in the form of a 2% aqueous solution of not more than 15 centipoise at 20° C.;
   (2) a component selected from the group consisting of methanol, ethanol, isopropanol, 1-propanol, and/or acetone and mixtures of two or more of the foregoing,
   (3) a surfactant selected from the group consisting of sorbitan fatty acid esters, sucrose fatty acid esters, polyoxyethylene fatty acid esters, and sodium lauryl sulfate;
   (4) water, wherein the proportion of component (2) and water (4) is in a range of from 40:60 to 60:40% by weight;
   forming a continuous band locally at the juncture of the cap and body edge of the capsule with the banding composition; and
   drying the sealed capsule.

2. The method according to claim 1, wherein the low viscosity HPMC is present in the banding composition in an amount of more than 20% by weight based on the entire weight of the banding composition.

3. The method according to claim 1, wherein the component (2) is selected from acetone, ethanol and mixtures thereof.

4. The method according to claim 1, wherein component (2) is ethanol, the surfactant is sorbitan monolaurate, and the proportion of component (2) and water (4) is 50:50% by weight.

5. The method according to claim 1, wherein the low viscosity HPMC is a HPMC having a viscosity, in the form of a 2% aqueous solution, of not more than 4.5 centipoise at 20° C.

6. The method according to claim 1, further comprising distributing the banding composition between overlapping sections of the cap and the body.

7. A method for sealing a hard capsule having a body and a cap, comprising:
   contacting a juncture of the body and the cap with a banding composition, the banding composition comprising
   (1) low viscosity hydroxypropylmethyl cellulose (HPMC), wherein the low viscosity HPMC has a viscosity of not more than 4.5 centipoise at 20° C. as determined for a 2% aqueous solution and the HPMC is present in the banding composition in an amount of more than 15% by weight based on the entire weight of the banding composition, (2) a component selected from the group consisting of methanol, ethanol, isopropanol, 1-propanol, acetone and mixtures of two or more of the foregoing, wherein component (2) is in an amount of more than 30% by weight and less than 60% by weight based on the entire weight of the banding composition, (3) sorbitan monolaurate, and (4) water, wherein the water is in an amount of more than 30% by weight and less than 60% by weight based on the entire weight of the banding composition, and wherein the proportion of component (2) and water is in a range of from 40:60 to 60:40% by weight; forming a continuous band locally at the juncture of the cap and body edge of the capsule with the banding composition; and drying the continuous band on the capsule.

8. The method of claim 7, wherein the contacting is performed at room temperature.

9. The method of claim 7, wherein the low viscosity HPMC has a viscosity in the form of a 2% aqueous solution of from 3 centipoise to 4.5 centipoise at 20° C.

10. The method of claim 7, wherein the low viscosity HPMC is present in the banding composition in an amount of from 15% to 24% by weight based on the entire weight of the banding composition.

11. The method of claim 1, wherein the contacting is carried out at room temperature.

12. The method of claim 1, wherein the low viscosity HPMC has a viscosity in the form of a 2% aqueous solution of from 3 centipoise to 15 centipoise at 20° C.

13. The method of claim 1, wherein the low viscosity HPMC has a viscosity in the form of a 2% aqueous solution of from 4.5 centipoise to 15 centipoise at 20° C.

14. The method of claim 1, wherein the low viscosity HPMC has a viscosity in the form of a 2% aqueous solution of from 6 centipoise to 15 centipoise at 20° C.

15. The method of claim 1, wherein the low viscosity HPMC is present in the banding composition in an amount of from 15% to 24% by weight based on the entire weight of the banding composition.

16. A method for banding a hydroxypropylmethyl cellulose (HPMC) hard capsule having a body and a cap with the inner circumference of said cap at its edge being greater than the outer circumference of the capsule body, said method comprising:

providing said HPMC hard capsule; and contacting the juncture of the cap and body edge of said HPMC hard capsule with a banding composition, the banding composition comprising:

(1) low viscosity HPMC present in the banding composition in an amount of more than 15% by weight based on the entire weight of the banding composition, the low viscosity HPMC having a viscosity in the form of a 2% aqueous solution of not more than 15 centipoise at 20° C.;

(2) a component selected from the group consisting of methanol, ethanol, isopropanol, 1-propanol, and/or acetone and mixtures of two or more of the foregoing, (3) a surfactant selected from the group consisting of sorbitan fatty acid esters, sucrose fatty acid esters, polyoxyethylene fatty acid esters, and sodium lauryl sulfate;

(4) water;

forming a continuous band locally at the juncture of the cap and body edge of the capsule with the banding composition; and drying the sealed capsule.

17. The method of claim 16, wherein the contacting is carried out at room temperature.

18. The method of claim 16, wherein the low viscosity HPMC has a viscosity in the form of a 2% aqueous solution of from 3 centipoise to 15 centipoise at 20° C.

19. The method of claim 16, wherein the low viscosity HPMC has a viscosity in the form of a 2% aqueous solution of from 4.5 centipoise to 15 centipoise at 20° C.

20. The method of claim 16, wherein the low viscosity HPMC is present in the banding composition in an amount of from 15% to 24% by weight based on the entire weight of the banding composition.

* * * * *